(12) United States Patent
Chernyak et al.

(10) Patent No.: US 7,040,759 B2
(45) Date of Patent: May 9, 2006

(54) APPARATUS AND METHOD FOR DETERMINING RELATIVE POSITIONAL AND ROTATIONAL OFFSETS BETWEEN A FIRST AND SECOND IMAGING DEVICE

(75) Inventors: Dimitri Chernyak, Sunnyvale, CA (US); Jeffrey J. Persoff, San Jose, CA (US)

(73) Assignee: VISX, Incorporated, Santa Clara, CA (US)

( * ) Notice: Subject to any disclaimer, the term of this patent is extended or adjusted under 35 U.S.C. 154(b) by 336 days.

(21) Appl. No.: 10/365,121

(22) Filed: Feb. 11, 2003

(65) Prior Publication Data

US 2003/0151720 A1    Aug. 14, 2003

Related U.S. Application Data

(60) Provisional application No. 60/356,658, filed on Feb. 11, 2002.

(51) Int. Cl.
  *A61B 3/00* (2006.01)
  *A61B 3/10* (2006.01)
  *G06K 9/36* (2006.01)
  *G06K 9/32* (2006.01)

(52) U.S. Cl. .............. 351/246; 351/205; 351/206; 351/221; 382/287; 382/294

(58) Field of Classification Search ........... 351/200, 351/205, 206, 209, 221, 246; 382/110, 117, 382/118, 190, 184, 286, 287, 289, 291, 293, 382/294, 295, 296; 606/4–6; 396/18, 51
See application file for complete search history.

(56) References Cited

U.S. PATENT DOCUMENTS

| | | | | |
|---|---|---|---|---|
| 3,600,098 A | * | 8/1971 | Mohrman | 356/153 |
| 3,614,238 A | * | 10/1971 | Stites | 356/124 |
| 4,580,042 A | * | 4/1986 | Tokutomi et al. | 250/201.8 |
| 4,640,619 A | * | 2/1987 | Edmark, III | 356/625 |
| 4,672,676 A | * | 6/1987 | Linger | 382/141 |
| 5,220,176 A | * | 6/1993 | Kawai | 250/548 |
| 5,648,854 A | * | 7/1997 | McCoy et al. | 356/399 |
| 5,655,030 A | * | 8/1997 | Suzuki | 382/152 |
| 5,818,954 A | | 10/1998 | Tomono et al. | |
| 5,857,120 A | | 1/1999 | Konishi | |
| 5,960,125 A | * | 9/1999 | Michael et al. | 382/294 |
| 6,152,563 A | | 11/2000 | Hutchinson et al. | |
| 6,175,750 B1 | * | 1/2001 | Cook et al. | 600/310 |
| 6,271,895 B1 | | 8/2001 | Takagi et al. | |
| 6,343,143 B1 | * | 1/2002 | Guillemaud et al. | 382/130 |
| 6,396,961 B1 | * | 5/2002 | Wixson et al. | 382/294 |
| 6,637,884 B1 | | 10/2003 | Martino | |
| 6,671,049 B1 | * | 12/2003 | Silver | 356/401 |

* cited by examiner

*Primary Examiner*—Eric F. Winakur
*Assistant Examiner*—John R. Sanders
(74) *Attorney, Agent, or Firm*—Townsend&Townsend&CrewLLP; Mark D. Barrish

(57) ABSTRACT

Apparatus and methods can determine positional and rotational offsets between a first and second imaging device. Embodiments may determine the relative offsets between a Hartmann-Shack wavefront sensor and a pupil camera using a calibration apparatus having a rotationally asymmetric aperture. The image obtained by the Hartmann-Shack wavefront sensor way comprise a spot pattern that corresponds to a shape of the aperture. A marker may be superimposed over the images, with a shape of the marker substantially corresponding to the shape of the aperture, and movements of the marker from nominal positions on each image can be compared to determine the offsets.

26 Claims, 13 Drawing Sheets

APPARATUS AND METHOD FOR DETERMINING RELATIVE POSITIONAL AND ROTATIONAL OFFSETS BETWEEN A FIRST AND SECOND IMAGING DEVICE

CROSS-REFERENCES TO RELATED APPLICATIONS

The present application claims benefit of Provisional Patent Application No. 60/356,658, entitled "Apparatus and Method for Determining Relative Positional and Rotational Offsets Between a First and Second Imaging Device," filed Feb. 11, 2002, the complete disclosure of which is incorporated herein by reference.

The present application is also related to Provisional Patent Application No. 60/356,657, entitled "Method and Device for Calibrating an Optical Wavefront System," and Provisional Patent Application No. 60/356,672, entitled "Closed Loop System and Method for Ablating Lenses with Aberrations" both filed on Feb. 11, 2002, the complete disclosures of which are incorporated herein by reference.

BACKGROUND OF THE INVENTION

The present application relates generally to registering a first image device with a second image device. More particularly, the present invention relates to an apparatus and a method for determining a relative positional and rotational offsets between a first and second imaging device of a wavefront system.

Laser eye surgical procedures typically employ some sort of system that may measure the optical characteristics of the patient's eye. One promising eye measurement system is the VISX WaveScan™ System, which uses a Hartmann-Shack wavefront sensor assembly that may quantify higher-order aberrations throughout the entire optical system, including first and second-order sphero-cylindrical errors and third through sixth-order aberrations caused by coma and spherical aberrations. The wavefront measurement of the eye creates a high order aberration map that permits assessment of aberrations throughout the optical pathway of the eye, e.g., both internal aberrations and aberrations on the corneal surface. Thereafter, the wavefront aberration information may be saved and thereafter input into the laser system to compute a custom ablation pattern to correct the aberrations in the patient's eye.

The WaveScan™ System also includes a camera ("pupil camera") that takes images of the eye at the time the wavefront measurements are taken with the Hartmann-Shack wavefront sensor assembly. The images of the eye taken with the pupil camera may be used to track the spatial position of the eye so as to properly align the ablative laser with the eye during the corneal ablation treatment.

Because the tracking and alignment of the eye during the laser ablation is based on the image taken with the pupil camera, it is important that the wavefront data is spatially aligned, both translationally and rotationally, with the image taken with the pupil camera. If the pupil camera and wavefront sensor are not spatially aligned when the wavefront measurements are obtained, the subsequent laser assisted corneal ablation, which relies on the wavefront measurements, may not be properly registered with the patient's eye.

Consequently, what are needed are devices and methods which may determine a relative positional and rotational offset between the two imaging devices of the wavefront system.

BRIEF SUMMARY OF THE INVENTION

The present invention measures the relative positional and rotational offset between the Hartmann-Shack camera and pupil camera of the wavefront system and calibrates the two cameras of the wavefront system.

The present invention may use computer implemented software algorithms to correct residual errors between the position and rotation of the Hartmann-Shack sensor and the pupil camera so that the images taken with the two imaging devices may be properly aligned, relative to each other. Once the positional and rotational offset of the Hartmann-Shack sensor and pupil camera are determined, the offset values may be stored in a memory of the system so that the software may correct the misalignment between the images taken with the cameras. Typically, the methods of the present invention may be used to calibrate the wavefront system during manufacturing or during periodic services of the wavefront system to ensure that the two imaging devices are spatially aligned during use in the field.

It should be appreciated however, that while the following description focuses on spatially aligning the Hartmann-Shack sensor and pupil camera of a wavefront system, that the present invention may be used to spatially align any two (or more) imaging devices which concurrently record images.

In one aspect, the present invention provides a calibration apparatus for determining a relative positional and rotational offset between a Hartmann-Shack camera and a pupil camera. The apparatus comprises a body having an aperture. In some embodiments, the aperture is rotationally asymmetric. The rotationally asymmetrical aperture may take a variety of asymmetric forms. In one useful embodiment, the asymmetrical aperture is in the form of a cross or X. In some configurations, the apparatus may include means for preventing direct light reflections off of the body of the apparatus. In other configurations the aperture may be movably coupled to the body so as to allow for rotation and translation of the aperture relative to the body. The apparatus may be positioned in the imaging plane of the Hartmann-Shack camera and pupil camera so that it is concurrently imaged by both of the cameras. The image of the apparatus may be used to measure and compensate for the positional and rotational offsets between the two cameras.

In a further aspect, the present invention provides a method of registering or calibrating a first imaging device with a second imaging device. The methods generally comprise positioning a calibration apparatus or fixture so that the fixture is imaged by the first imaging device and second imaging device. The images of the fixture obtained by the first imaging device and the second imaging device are analyzed to determine a misalignment between the first imaging device and the second imaging device.

A variety of fixtures may be used with the methods and systems of the present invention to measure and correct the misalignment between the first and second imaging devices. For example, in some embodiments a fixed, non-adujstable calibration apparatus may be used. In other embodiments, a fully adjustable calibration apparatus may be used so as to allow a user to adjust a rotational orientation and translational position of at least a portion of the calibration apparatus.

In one embodiment, the method comprises providing a calibration apparatus or fixture that includes a body having a rotationally asymmetric aperture. The fixture is positioned in an optical path of the first imaging device and a second imaging device. An image of the fixture is obtained by the first imaging device and second imaging device. Light may be directed through the rotationally asymmetric aperture to the first imaging device and second imaging device and the aperture is imaged with the first imaging device and the second imaging device to determine the positional and rotational offsets. The first imaging device may be a Hartmann-Shack camera that measures wavefront data. Optionally, the aperture may be adjustable.

A marker or overlay may be superimposed over at least one of the images of the fixture taken with the first and second imaging device. The marker in the image obtained with the first imaging device is moved from a nominal position (e.g., a center of the image) to substantially align the marker with the fixture. The movement information (e.g., movement along the x-axis and y-axis and rotation about the z-axis) of the marker in the first image is saved for future reference. The marker in the image obtained with the second imaging device is moved from a nominal position (e.g., a center of the image) to substantially align the marker with the fixture. The movement information of the marker in the second image is also saved for future reference. Finally, the movement information of the marker in the first image is compared with the movement information of the marker in the second image to determine the rotational and positional offset between the first and second imaging devices.

In another embodiment, the fixture may be imaged by the first imaging device and the second imaging device. A translational position and rotational orientation of the fixture may be adjusted until the fixture is positioned in a desired position in the image obtained by the first imaging device, such as a center of the image. Once the fixture is in the desired position, the image obtained by the second imaging device is analyzed to determine if the fixture is in the same desired position (e.g., a center of the image obtained by the second imaging device). If the fixture is not in the desired position, a marker that is overlayed over the image that is obtained by the second imaging device may be moved from the desired position until it is substantially aligned with the fixture. The movement information of the marker may then be used to determine the rotational and positional offset between the first and second imaging devices.

In yet another aspect, the present invention provides a system which comprises an imaging system that has a Hartmann-Shack camera and a pupil camera. A calibration apparatus, such as a body comprising a rotationally asymmetric aperture may be positioned in an optical path of the Hartmann-Shack camera and pupil camera. A control system is coupled to the Hartmann-Shack camera and pupil camera to determine the relative position of the calibration apparatus in the images taken with each of the cameras so as to determine the misalignment between the two cameras.

In one embodiment, the control system has a first and a second mode. The control system in the first mode may be configured to superimpose a marker in a nominal position over an image of the calibration apparatus taken with the Hartmann-Shack camera and an image taken with the pupil camera. The marker maybe allowed to be moved into substantial alignment with the image of the asymmetric aperture. In the second mode, the control system may compare the type of movement of the marker in the image taken with the Hartmann-Shack camera with the type of movement of the marker in the image taken with the pupil camera so as to determine the positional and rotational offset between the Hartmann-Shack camera and the pupil camera.

In another aspect, the present invention provides code modules and graphical user interfaces for carrying out the methods of the present invention that are described herein.

These and other aspects will be apparent in the remainder of the figures, description and claims.

DETAILED DESCRIPTION OF THE INVENTION

The present invention is particularly useful for enhancing the accuracy and efficacy of laser eye surgical procedures, such as photorefractive keratectomy (PRK), phototherapeutic keratectomy (PTK), laser in situ keratomileusis (LASIK), and the like. Preferably, the present invention mayprovide enhanced optical accuracy of refractive procedures by improving the methodology for deriving and aligning a corneal ablation or other refractive treatment program with the patient's eye.

While the system and methods of the present invention are described primarily in the context of a laser eye surgery system, it should be understood that the techniques of the present invention may be adapted for use in alternative eye treatment procedures and systems such as radial keratotomy, intraocular lenses, corneal ring implants, collagenous corneal tissue thermal remodeling, and the like.

Figure 1:
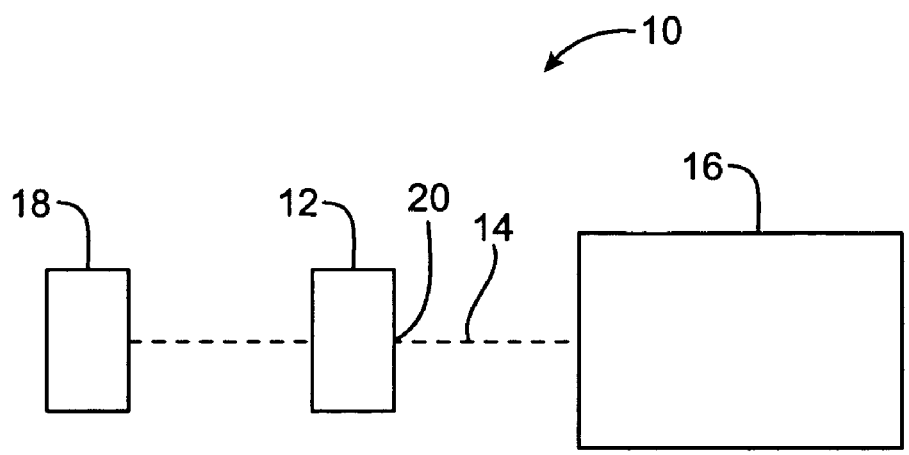
FIG. 1 schematically illustrates a wavefront system, calibration apparatus, and a target embodied by the present invention.

FIG. 1 schematically illustrates a calibration system 10 of the present invention. Calibration system 10 includes a reference object, such as a fixture or calibration apparatus 12 that is positioned in an optical path 14 of wavefront system 16 between wavefront system 16 and a target 18. Wavefront system 16 may comprise inter alia a Hartmann-Shack camera and a pupil camera for simultaneously obtaining wavefront data and an image of the eye, respectively.

Light maybe emitted from a light source (not shown) in wavefront system 16, through an aperture 20 in calibration apparatus 12 and directed onto target 18. Target 18 maybe used to create a point source for the Hartmann-Shack camera and the pupil camera. A generated or reflected light may be directed from target 18 back through aperture 20 of calibration apparatus 12 and into the wavefront system 16. As the calibration apparatus 12 is placed in the imaging plane of the Hartmann-Shack camera, a spot pattern that corresponds to a shape of the aperture 20 in calibration apparatus 12 appears in the image obtained by the Hartmann-Shack camera. In one embodiment, aperture 20 is rotationally asymmetric. In other embodiments, however, the aperture may be rotationally symmetric, if desired. The position and orientation of calibration apparatus 12 is determined in both of the images to estimate the misalignment between the cameras.

In one configuration, the target 18 may have matte white surface so as to reduce the amount of unwanted light reflections. In another configuration, target 18 comprises Spectralon®, which may reflect optically diffuse light back through the calibration apparatus 12. It should be appreciated however, that a variety of other materials may be used as a target to reflect or to generate light back through the calibration apparatus 12.

Figure 2:
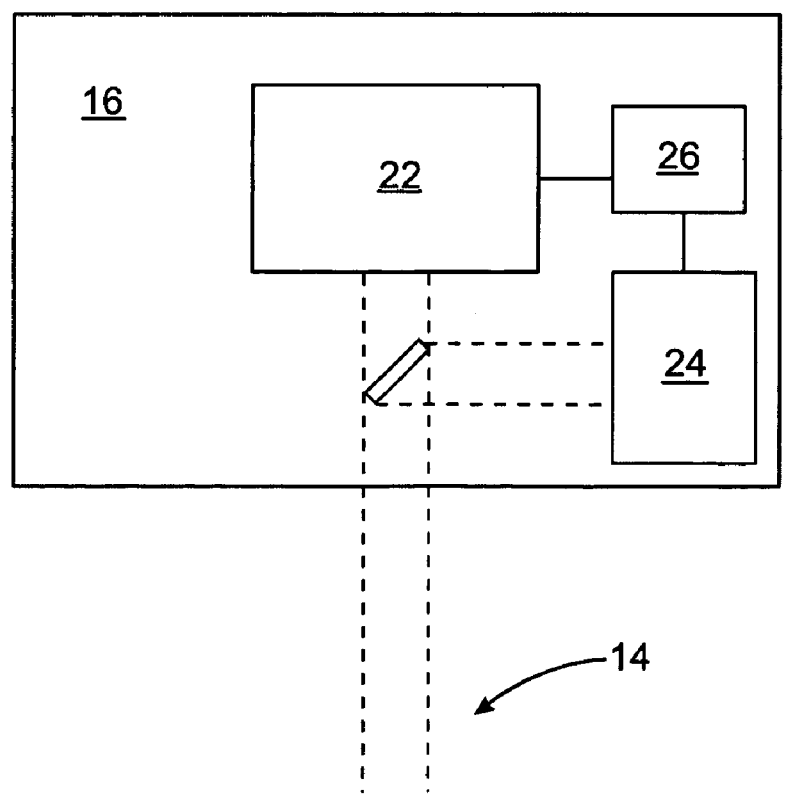
FIG. 2 schematically illustrates a simplified wavefront system of the present invention.

FIG. 2 schematically illustrates a simplified wavefront system 16 of the present invention. Wavefront system 16 generally includes a Hartmann-Shack camera 22 that is configured to obtain a wavefront measurement of the optical tissues of a patient's eye. Hartmann-Shack camera 22 has a lenslet array (not shown) that records a deviation of rays from a point source on the retina. Wavefront system 16 also includes a pupil camera 24, such as a CCD, that is configured to simultaneously records an image of the patient's eye at the time of the wavefront measurement by the Hartmann-Shack camera. A controller, such as a computer system 26 may be coupled to cameras 22, 24 for analyzing and calibrating the images obtained by the cameras 22, 24. Computer system 26 may be incorporated into the wavefront system 16, or it may be a separate computer that is coupled to cameras 22, 24.

Figure 3:
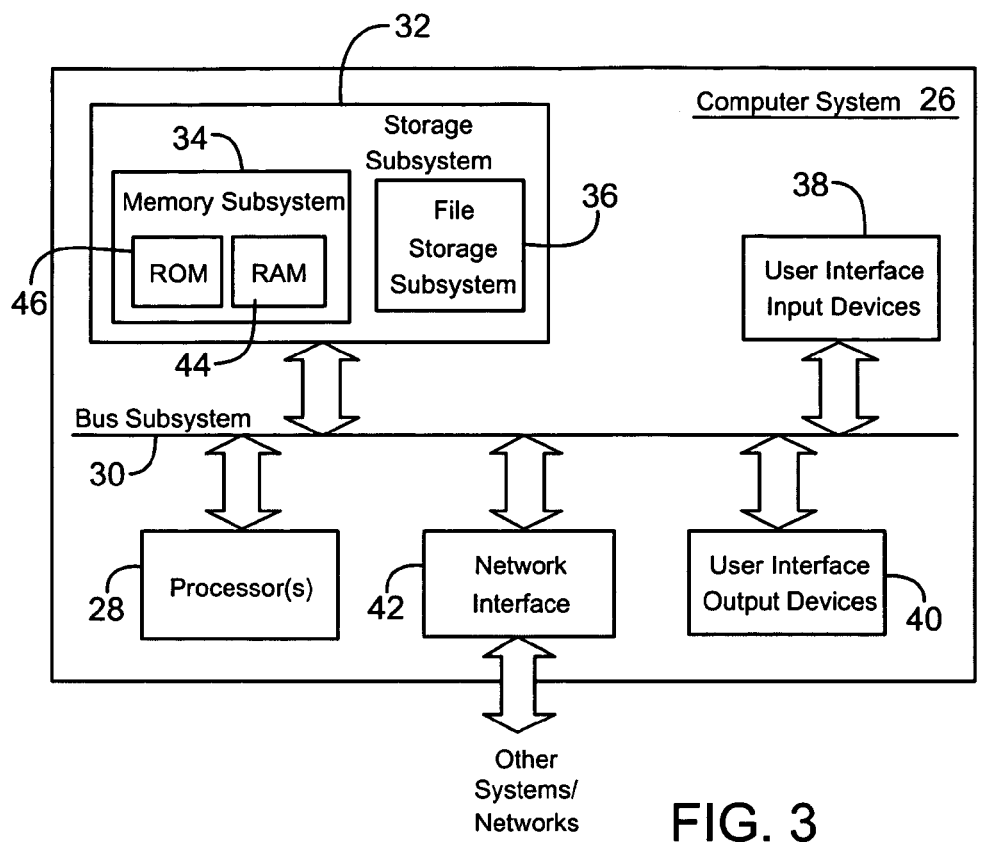
FIG. 3 schematically illustrates a simplified computer system of the present invention.

FIG. 3 is a simplified block diagram of a computer system 26 that may used to align and register the images obtained with cameras 22, 24 according to an embodiment of the present invention. Computer system 26 includes at least one processor 28, which communicates with a number of peripheral devices via a bus subsystem 30. These peripheral devices may include a storage subsystem 32, comprising a memory subsystem 34 and a file storage subsystem 36, user interface input devices 38, user interface output devices 40, and an optional network interface subsystem 42. The input and output devices allow user interaction with computer system 26. A user may be a human user, a device, a process, another computer, and the like.

Network interface subsystem 42 provides an interface to other computer systems and communication networks. Embodiments of network interface subsystem 42 include an Ethernet card, a modem (telephone, satellite, cable, ISDN, etc.), (asynchronous) digital subscriber line (DSL) units, and the like. The computer networks may include the Internet, local area networks (LANs), wide area networks (WAN), wireless networks, intranets, private networks, public networks, switched networks, and the like.

User interface input devices 38 may include a keyboard, pointing devices such as a mouse, trackball, touchpad, or graphics tablet, a scanner, a barcode scanner, a touchscreen incorporated into the display, audio input devices such as voice recognition systems, microphones, and other types of input devices. In general, use of the term "input device" is intended to include all possible types of devices and ways to input information using computer system 26.

User interface output devices 40 may include a display subsystem, a printer, a fax machine, or non-visual displays such as audio output devices. The display subsystem may be a cathode ray tube (CRT), a flat-panel device such as a liquid crystal display (LCD), or a projection device. In general, use of the term "output device" is intended to include all possible types of devices and ways to output information from computer system 26.

Storage subsystem 32 may be configured to store the basic software programming and data constructs that provide the functionality of the present invention. For example, according to an embodiment of the present invention, software modules implementing the functionality of the present invention may be stored in storage subsystem 32. These software modules may be executed by processor(s) 28. In a distributed environment, the software modules may be stored on a plurality of computer systems and executed by processors of the plurality of computer systems. Storage subsystem 32 may also provide a repository for storing various databases and data structures that may be used to store information according to the teachings of the present invention. Storage subsystem 32 may comprise memory subsystem 34 and file storage subsystem 36.

Memory subsystem 34 may include a number of memories including a main random access memory (RAM) 44 for storage of instructions and data during program execution and a read only memory (ROM) 46 in which fixed instructions are stored. File storage subsystem 36 provides persistent (non-volatile) storage for program and data files, and may include a hard disk drive, a floppy disk drive along with associated removable media, a Compact Digital Read Only Memory (CD-ROM) drive, an optical drive, removable media cartridges, CD, DVD, and other like storage media. One or more of the drives may be located at remote locations on other connected computers.

Bus subsystem 30 provides a mechanism for letting the various components and subsystems of computer system 26 communicate with each other as intended. The various subsystems and components of computer system 26 need not be at the same physical location but may be distributed at various locations. Although bus subsystem 30 is shown schematically as a single bus, alternative embodiments of the bus subsystem may utilize multiple busses.

Computer system 26 itself may be of varying types including a personal computer, a portable computer, a workstation, a computer terminal, a network computer, a mainframe, or any other data processing system. Due to the ever-changing nature of computers, the description of computer system 26 depicted in FIGS. 2 and 3 is intended only as a specific example for purposes of illustrating one embodiment of the present invention. Many other configurations of a computer system are possible having more or fewer components than the computer system depicted in FIG. 3.

Figure 4:
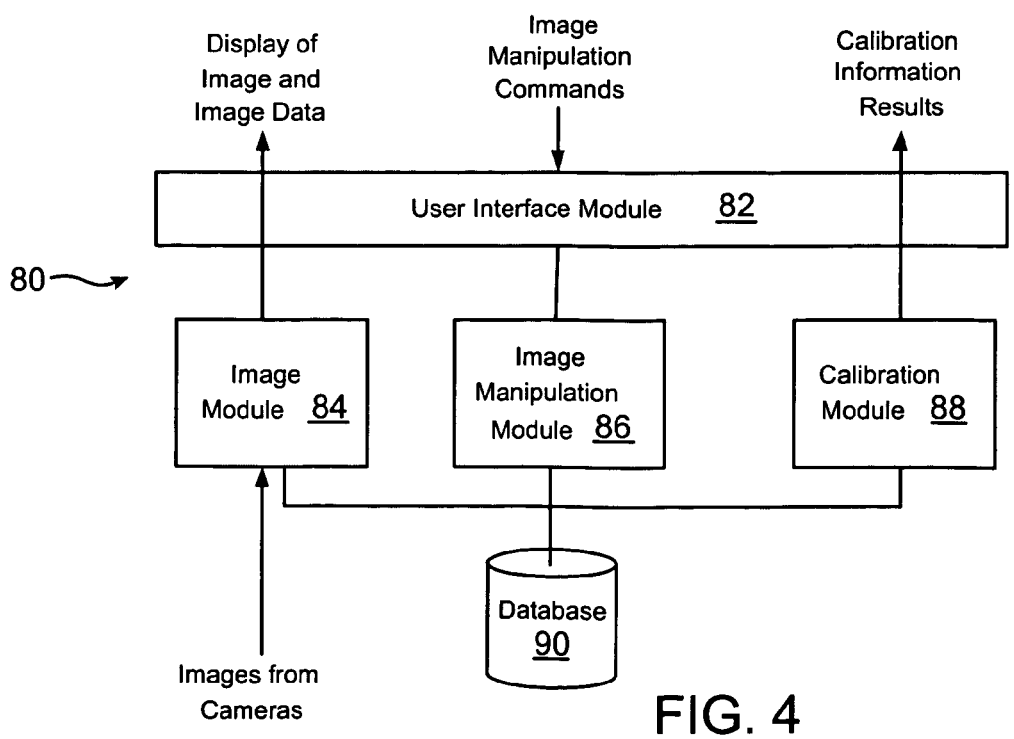
FIG. 4 illustrates some modules which may carry out the methods of the present invention.

FIG. 4 depicts a simplified block diagram of some modules that carry out the methods of the present invention. The modules may be implemented in software, hardware, or a combination thereof within wavefront system 16. In the embodiment depicted in FIG. 4, modules 80 comprise a user interface module 82, an image module 84, image manipulation module 86, and a calibration module 88.

User interface module 82 provides an interface via which a user may input commands, view images, and view the results of the calibration. The user may input commands to manipulate the images to assist in the determination of the rotational orientation and position of the calibration apparatus in the images obtained by the Hartmann-Shack camera 22 and pupil camera 24.

According to an embodiment of the present invention, images of the calibration module are obtained by image module 84 from cameras 22, 24. The images may be stored in a database 90, which may be located in a storage subsystem 32, a remote server, or the like. The user may specify which image is displayed by providing proper inputs into the user interface module 82. Once the appropriate image is displayed, image manipulation module 86 is configured to receive input commands via user interface module 82 to manipulate the image obtained by one of the cameras to determine the image parameters of the image obtained by the camera (e.g., orientation and positional offsets of the calibration apparatus). Once the first image is analyzed by image manipulation module 86, the image and parameter information of the first image may be stored in database 90. User interface module 82 may then be used to access image module 84 to view the second image (e.g., the image obtained by the other camera). Image manipulation module 86 may then instructed by the user through user interface module 82 to analyze and obtain the image parameters of the second image and store the second image and image parameters in database 90.

Once both of the images are analyzed by image manipulation module 86, calibration module 88 may be used to access the stored information in database 90 to determine the misalignment between the images obtained by cameras 22, 24. Calibration module 88 may be configured to output the calibration results of the calibration to user interface module 82 and optionally, automatically save the results in database 90 and automatically account for the misalignment. Alternatively, the results of the calibration may only be output to user interface module 82. User may then instruct calibration module 88 to save the calibration results in database 90. As can be appreciated, database 90 may be accessed by other modules (either local modules or remote modules) to allow the calibration information to be used in the wavefront system and/or a laser surgery system to compensate for any misalignment between cameras 22, 24.

The present invention also provides specific methods of registering images and compensating for a misalignment between a first imaging device (e.g., Hartmann-Shack camera 22) and second imaging device (e.g., pupil camera 24). If $(X^P, Y^P)$ are the pixel coordinates of the pupil camera 24, and $(X^{HS}, Y^{HS})$ are the pixel coordinates of the Hartmann-Shack camera 22, then there may be a projective transformation that relates the two coordinate systems of the Hartmann-Shack camera 22 and the pupil camera 24. A rigid transformation has been found to be sufficient to describe the relationship between the two cameras. Thus, the rigid transformation may be described by three parameters: $\Delta x$, $\Delta y$, and $\theta$, in which $\Delta x$ is the translation along an X-axis, $\Delta y$ is a translation along a Y-axis, and $\theta$ is a rotation about the Z-axis. A scale factor "A" between the Hartmann-Shack camera 22 and pupil camera 24 is a fixed value that is known. The transformation becomes:

$$\begin{bmatrix} X^P \\ Y^P \end{bmatrix} = A * \begin{bmatrix} \cos(\theta) & \sin(\theta) \\ -\sin(\theta) & \cos(\theta) \end{bmatrix} \begin{bmatrix} X^{HS} \\ Y^{HS} \end{bmatrix} + \begin{bmatrix} \Delta x \\ \Delta y \end{bmatrix}$$

In order to determine the values of the transformation parameters $\Delta x$, $\Delta y$, and $\theta$, a fixture or calibration apparatus 12 may be imaged by the Hartmann-Shack camera 22 and pupil camera 24 to determine the apparatus' position and orientation in the images of both cameras such that the spatial offsets of the cameras may be determined to subsequently estimate the transformation parameters.

Figure 5:
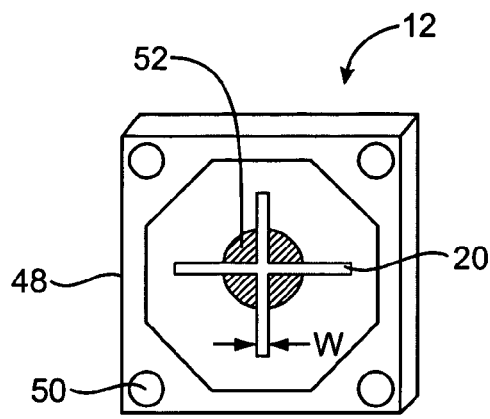
FIG. 5 shows an embodiment of a calibration apparatus incorporating the present invention.

FIG. 5 illustrates one calibration apparatus 12 that incorporates the present invention. Calibration apparatus 12 may be fixedly positioned on a WaveScan™ calibration rail (not shown) so as to position the calibration apparatus 12 in optical axis 14 of the wavefront system 16 (FIG. 1). It should be appreciated however, that a variety of other conventional attachment means may be used to position the calibration apparatus in the image plane of the WaveScan™ system or other wavefront systems, such as those manufactured and/or sold by Bausch & Lomb, Alcon Labs, and Wavefront Sciences. An aperture 20 is centered on a body 48 of calibration apparatus 12 so as to allow light to be reflected off of target 18 (FIG. 1) and back through the aperture and into the Hartmann-Shack camera 22 and pupil camera 24. Aperture 20 may be configured so that its width W in both dimensions corresponds to twice a spacing of a lenslets in the lenslets array in the Hartmann-Shack camera.

In exemplary embodiments, the aperture 20 is rotationally asymmetric and is in the shape of a cross that has an aperture width W of approximately 1 mm. The cross is one preferred embodiment since it has a clear central origin (e.g., the intersection between the horizontal aperture and vertical apertures). It should be appreciated however, that in other embodiments, the aperture may have any rotationally asymmetric shape, such as a line, a clover, a triangle, polygon, circle with markings, or the like, and may have other dimensions. If desired, calibration apparatus 12 may include a plurality of openings 50 for receiving the calibration rail (not shown).

Optionally, calibration apparatus 12 may include reflection prevention means 52 for preventing or reducing the direct reflection of light off of the body of the calibration apparatus 12. In the illustrated embodiment, a central portion 52 of the calibration device is covered with a non-reflective material or made of a non-reflective material so as to prevent light from reflecting off of calibration apparatus 12 and into the optical axis 14. In one embodiment, a central 8 mm diameter portion of the block is painted with a model railroad engine black die to prevent reflections. It should be appreciated, that in some embodiments, it may be possible to merely position calibration apparatus 12 at an angle relative to optical axis 14 to prevent light from being directly reflected off of the calibration apparatus along the optical axis 14 of the wavefront system 16.

Figure 6:
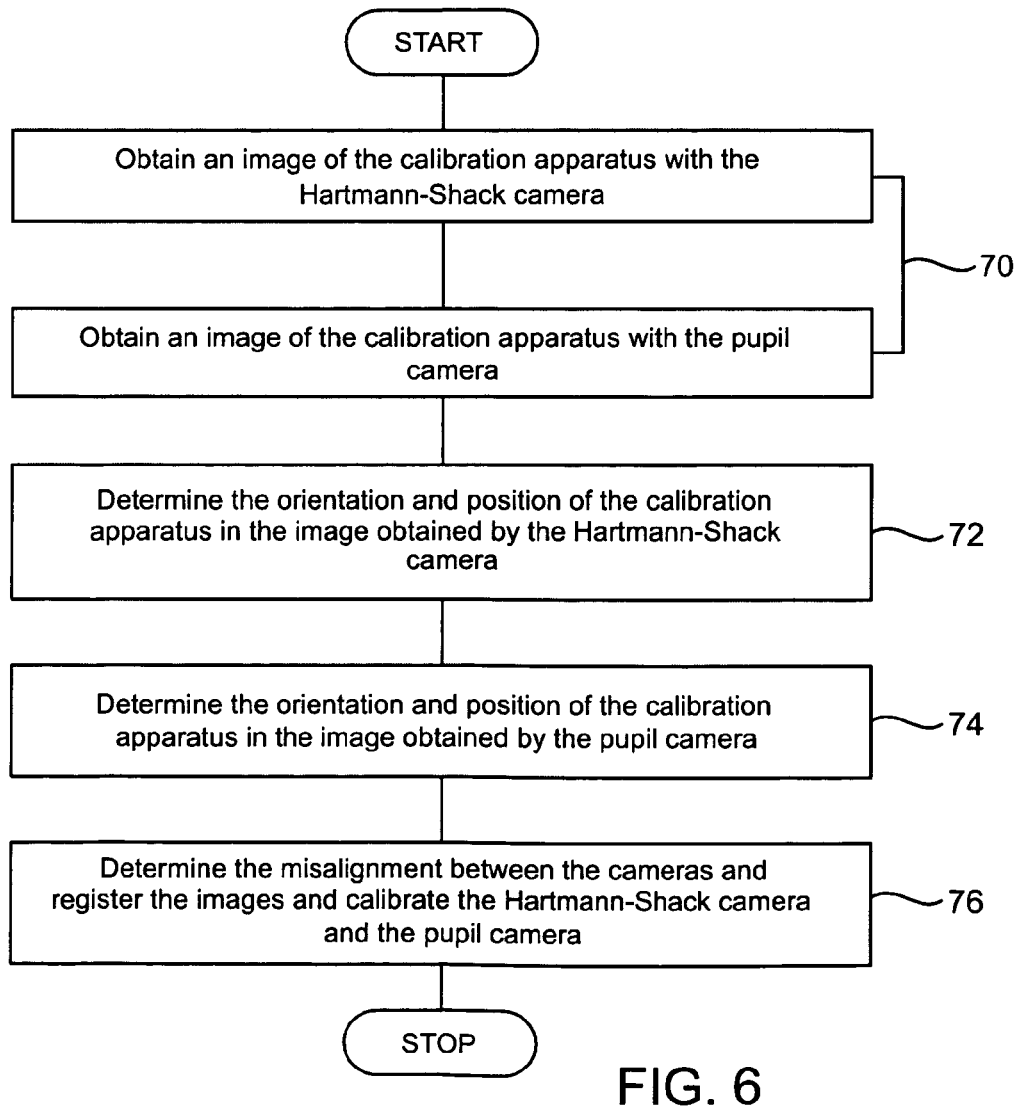
FIG. 6 schematically illustrates a simplified method of the present invention using the calibration apparatus of FIG. 5.

FIG. 6 schematically illustrates one simplified method of the present invention using the calibration apparatus of FIG. 5. First, images of the calibration apparatus are obtained with both the Hartmann-Shack camera and the pupil camera, step 70. The rotational orientation and position of the calibration apparatus is determined in the image obtained by the Hartmann-Shack camera, step 72. The rotational orientation and position of the calibration apparatus is also determined in the image obtained by the pupil camera, step 74. The positional and rotational parameters of the calibration apparatus in the images are compared with each other to determine any rotational and translational misaligmnents. The comparison of data may be used to determine the misalignment between the cameras and to register the images and calibrate the Hartmann-Shack camera and the pupil camera, step 76. Once the rotational and positional misalignments are determined, a software correction algorithm may be generated to correct for the misalignment between the cameras.

Figure 7:
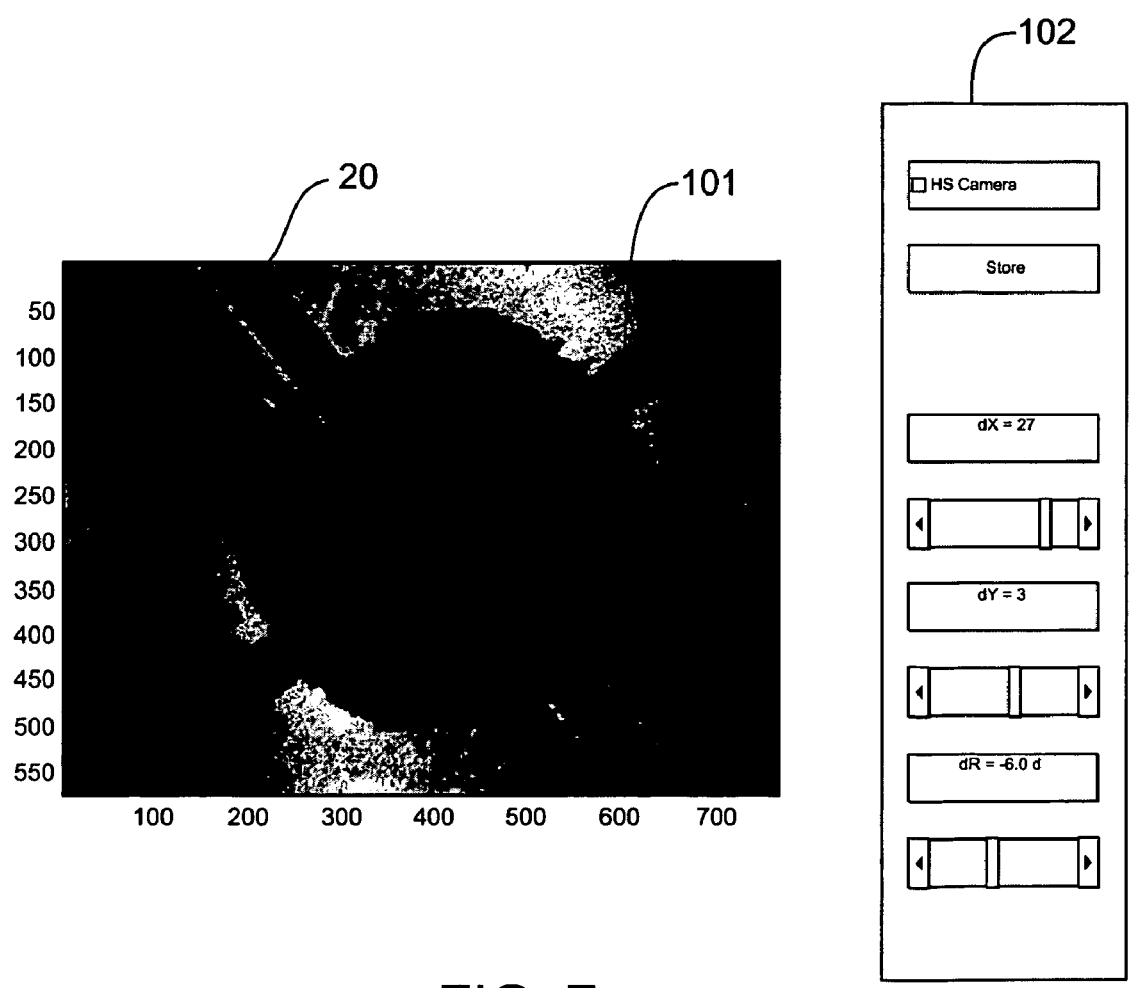
FIG. 7 shows an image of the calibration apparatus of FIG. 5 taken with a pupil camera.
Figure 8:
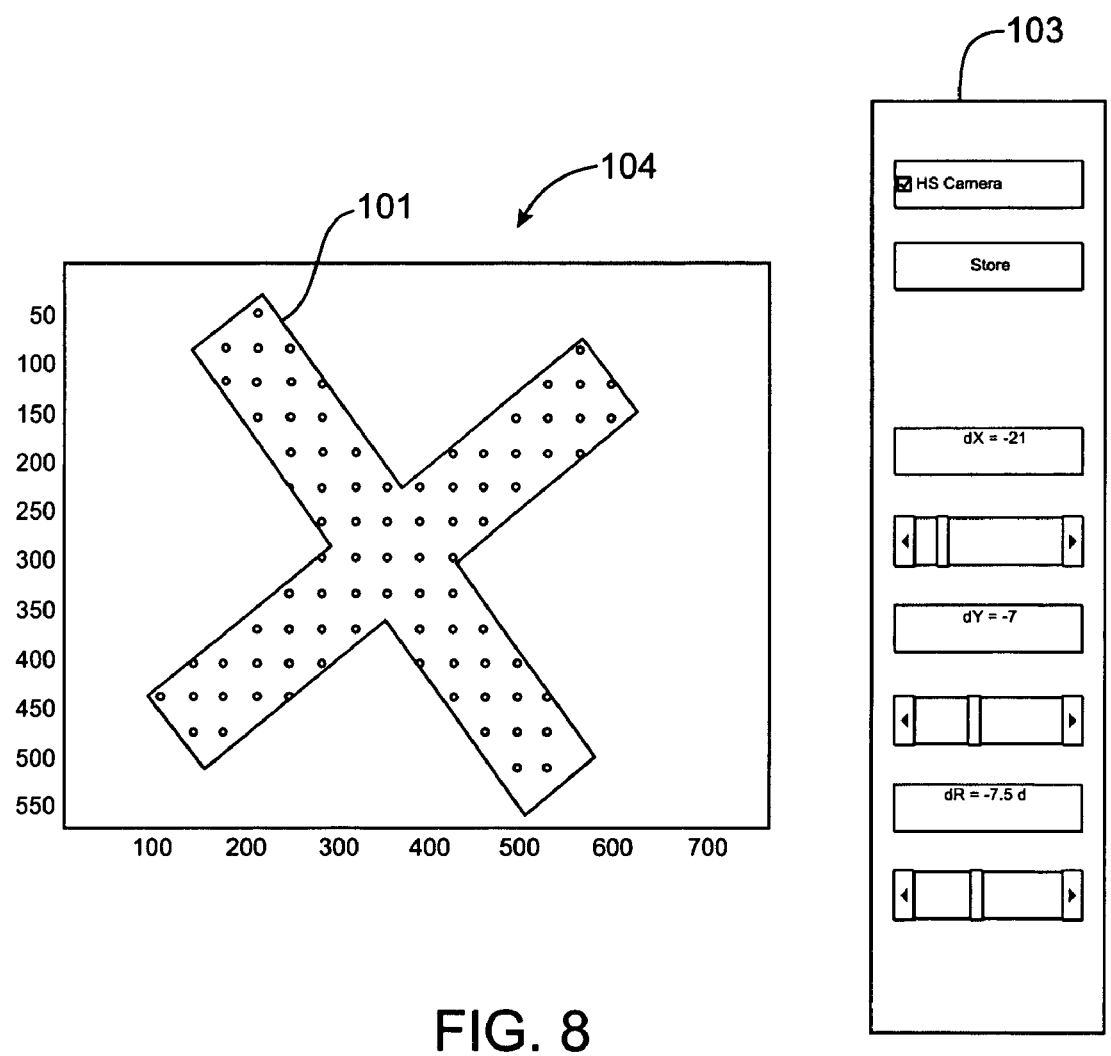
FIG. 8 shows an image of the calibration apparatus of FIG. 5 taken with a Hartmann-Shack camera.
Figure 9:
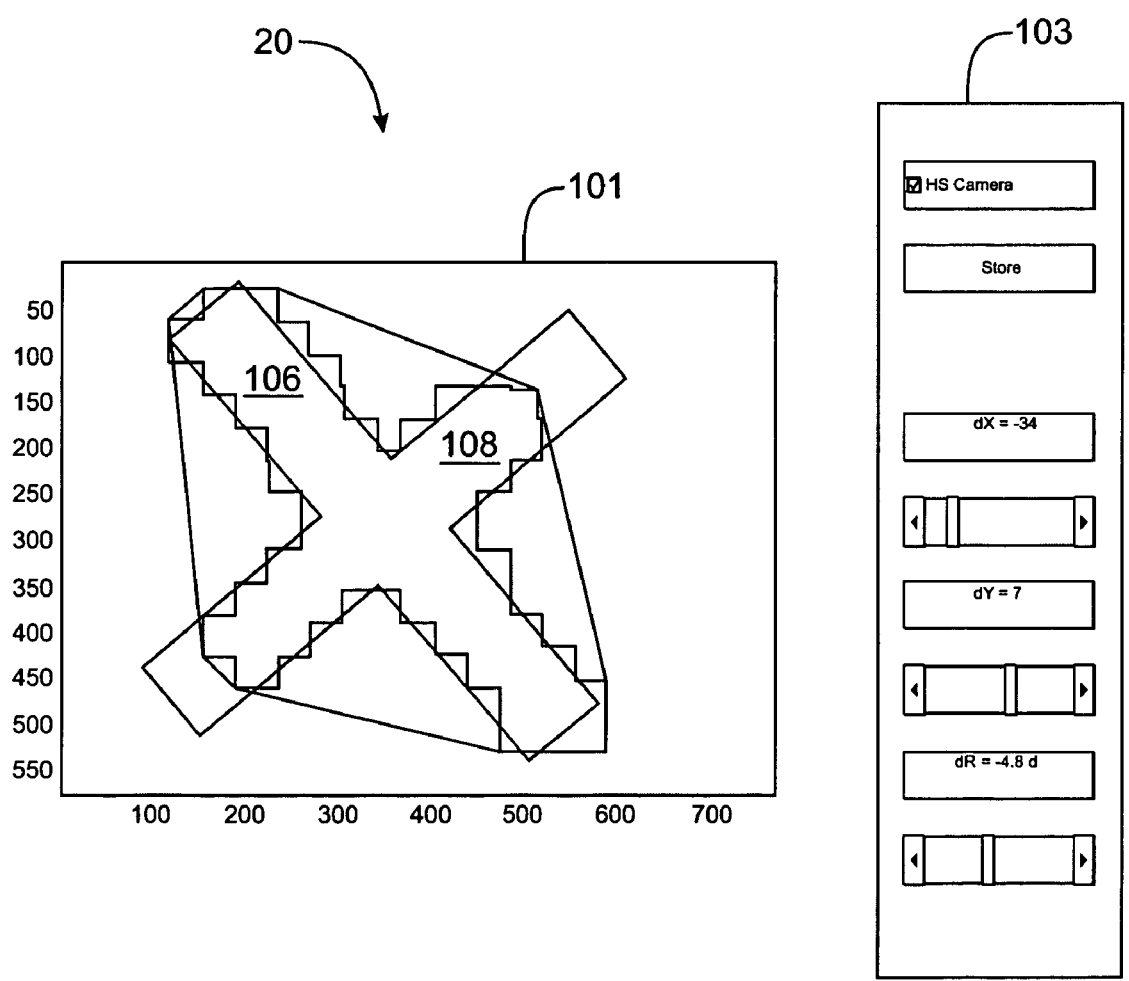
FIG. 9 shows a modified Hartmann-Shack image of the calibration apparatus of FIG. 5.

FIGS. 7 to 9 illustrate some simplified graphical user interfaces and images obtained by Hartmann-Shack camera 22 and pupil camera 24 as used with the calibration apparatus of FIG. 5. For example FIG. 7 illustrates an image of the calibration apparatus 12 taken by the pupil camera 24. Calibration software running on a computer system 26 (FIGS. 2 and 3) that is in communication with both cameras 22, 24 may superimpose a marker or overlay, such as a red cross image 100 (or another image that corresponds to the shape of aperture 20) in a nominal position on the image of aperture 20. In one configuration, the nominal position is a center of the image. In the illustrated embodiment, slider adjustments on the user interface 102 may allow the user to move the red cross image 100 along three parameters ($\Delta x$, $\Delta y$, and $\theta$) to substantially align the red cross image 100 with the image of the aperture 20. In the illustrated embodiment, positional adjustments may be done in 1-pixel steps while rotational adjustments may be done in ½ degree steps. As is shown on the slider adjustment, in this example, the red cross image 100 was moved 27 pixels in the x-direction, 3 pixels in the y-direction, and rotated −6.0° degrees from its original, nominal position to substantially align the overlay 100 with the asymmetric aperture 20. These values from the sliders, $\Delta x^{Pupil \to Object}$, $\Delta y^{Pupil \to Object}$, $\theta^{Pupil \to Object}$ are stored in a memory of computer system 26 for future reference. It should be appreciated however, that instead of slider adjustments a variety of other software means may be used to align the red cross image 100 with the image of the aperture 20. Moreover, instead of manually aligning the overlay with the image of aperture 20, the software modules of the present invention may be configured to automatically align the overlay with the image of aperture 20.

An image of the calibration apparatus 12 taken by the Hartmann-Shack camera 22 is shown in FIG. 8. As is known in the art, the image from a Hartmann-Shack camera will be in a form of a spot pattern 104. For ease of reference, the image has been thresholded at 10% of the maximum value to enhance the contrast of the spots from the lenslet array of the Hartmann-Shack sensor. Similar to the pupil camera, calibration software may superimpose a marker or overlay, such as a red cross image 101 or other images in a nominal position onto the image obtained with the Hartmann-Shack camera 22. User interface 103 may provide slider adjustments for three parameters ($\Delta x$, $\Delta y$, and $\theta$) to allow the user to substantially align the overlay red cross image with the spot image of the asymmetric aperture. As is shown on the slider adjustment, in this example, the red cross image 101 was moved −21 pixels in the x-direction, −7 pixels in the y-direction, and rotated −7.5° degrees to align the red cross 101 with the spot pattern image 104 of the aperture. In one configuration, positional adjustments may be done in 1-pixel steps and rotational adjustments may be done in ½ degree steps. In general, the red cross image 101 should be positioned so that it covers as many spots of the image of aperture 20 as possible. In all configurations, it may not be possible to cover all of the spots of the Hartmann-Shack image. The values from the sliders, $\Delta x^{HS \to Object}$, $\Delta y^{HS \to Object}$, $\theta^{HS \to Object}$, are stored in a memory of the system for future reference.

The next step in the calibration process is to establish the transformation parameters between the two cameras 22, 24. This may be accomplished by using the relative locations of an external object (e.g., the aperture of calibration apparatus 12) as a reference for both cameras. Therefore:

$$\Delta x = \Delta x^{Pupil \to Object} - \Delta x^{HS \to Object}$$

$$\Delta y = \Delta y^{Pupil \to Object} - \Delta y^{HS \to Object}$$

$$\theta = \theta^{Pupil \to Object} - \theta^{HS \to Object}$$

The above transformation parameters may be input into the transformation equation described above to determine the relative rotational and positional offsets such that the present invention may correct the residual alignment errors with software so as to allow the wavefront system to be accurately match the wavefront image with the image obtained with the pupil camera.

Thus, based on the above example:

$$\Delta x = 27 \text{ pixels} - (-21) \text{ pixels} = 48 \text{ pixels}$$

$$\Delta y = 3 \text{ pixels} - (-7) \text{ pixels} = 10 \text{ pixels}$$

$$\theta = -6.0 \text{ degrees} - (-7.5) \text{ degrees} = 1.5 \text{ degrees}$$

Consequently, in order to spatially align the wavefront elevational map taken with the Hartmann-Shack camera 22 with the images taken with the pupil camera 24, the software will have to shift the wavefront map 48 pixels in the +x-direction (e.g., to the right), 10 pixels in the +y direction (e.g. up), and 1.5 degrees about the z-axis (e.g., counter-clockwise).

While the alignment of the cross image 100 to the aperture image in the pupil image is locatable due to the visible edges of the aperture, the image from the Hartmann-Shack camera contains a spot pattern 104 that are visible through the aperture, but the edges or outside rows of spots may not be clearly visible. Thus, to simplify the alignment process of the cross image 101 to the Hartmann-Shack image of the aperture 20, an image processing algorithm that is stored in the memory of computer system 26 may be applied to the image from the Hartmann-Shack camera. In such embodiments, as shown in FIG. 9, the cross aperture of calibration apparatus 12 may be modified by shortening the length of one of the aperture arms so as to define a principal axis 106 and a secondary axis 108 on the cross aperture 20.

For example, the algorithm of the present invention may provide a thresholding step in which pixels that are at least 20% of the highest brightness value in the images are assigned a value of 1. The rest of the pixel values are set to zero. A block convolution step convolves the remaining image with square kernel of a size 40×40 containing 1's. This step may expand the spots to larger blocks so as to merge the "spots" (which are now larger blocks) together. Finally, the algorithm may include a morphological operation step in which the remainder of the binary image is analyzed to find the centroid and the principal axis. In one embodiment, the operations step may be carried out using Matlab's "imfeature" command. The value obtained from this step may be used to align the red cross image 10 with the altered image of the aperture 20.

Figure 10:
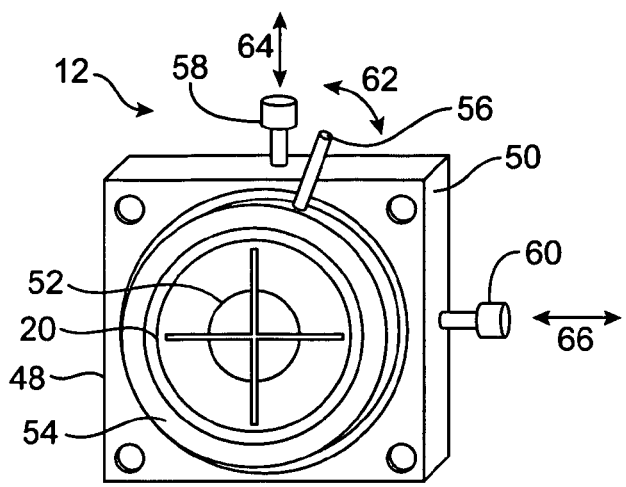
FIG. 10 shows another embodiment of a calibration apparatus that incorporates the present invention.

FIGS. 10–17 illustrate another embodiment of a calibration apparatus and a use of the calibration apparatus. FIG. 10 illustrates an adjustable embodiment of calibration apparatus 12 that includes a body 48 that may include one or more optional openings 50 for receiving the calibration rail. A rotatable and translatable body 54 having a centered cross-shaped aperture 20 is movably coupled to body 48. Calibration apparatus 12 may include a combination of one rotational adjustment member 56 and two translation members 58, 60 that allow for aperture rotational and positional adjustments, respectively. As noted by arrow 62, actuation of rotational adjustment member 56 rotates aperture 20 about its center. Actuation of translation member 58 may translate aperture 20 in the direction of arrow 64, while actuation of translation member 60 may translate aperture 20 in the direction of arrow 66. In one embodiment, translation members 58, 60 are screws such that rotation of the screws cause movement of translation members 58, 60 and body 54.

Figure 11:
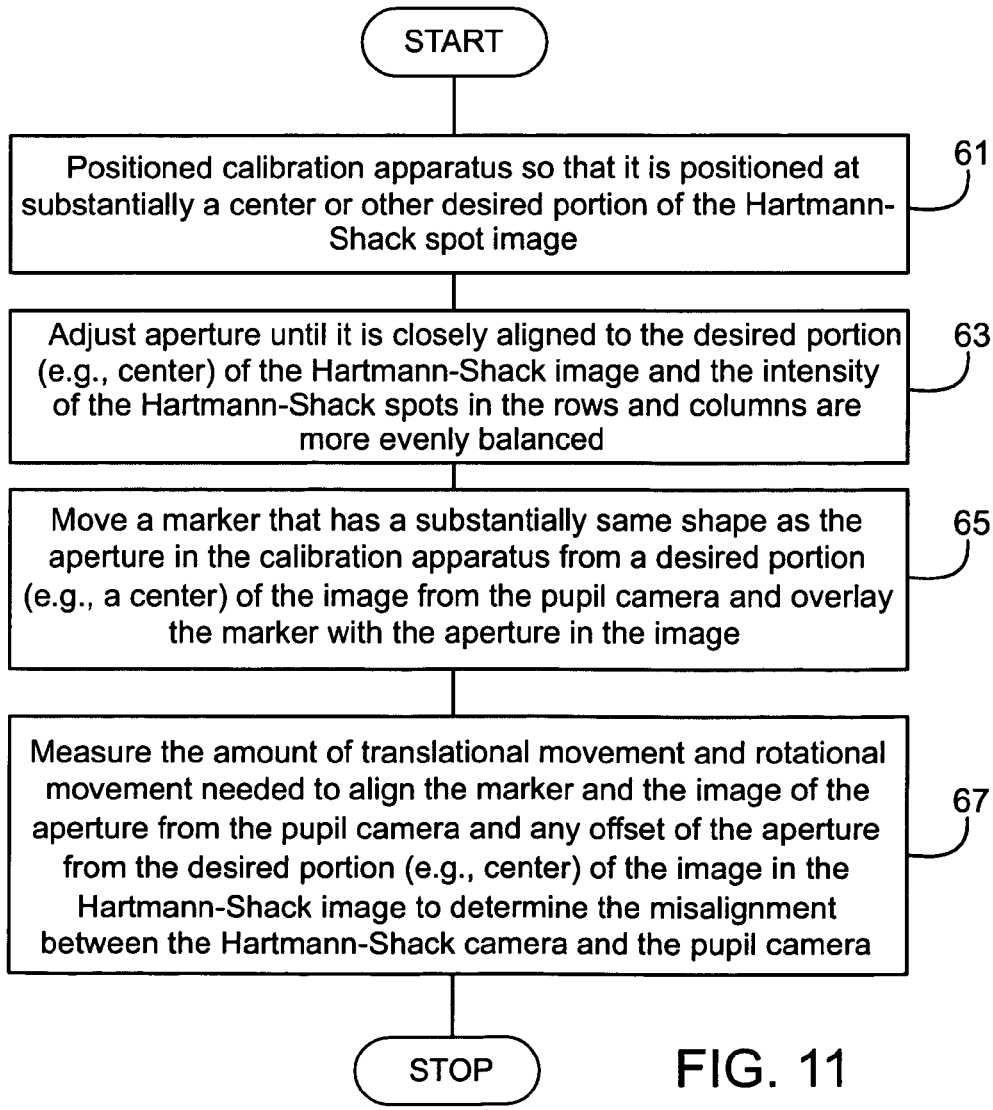
FIG. 11 schematically illustrates a simplified method of the present invention using the calibration apparatus of FIG. 10.

FIG. 11 schematically illustrates one simplified method of the present invention using the adjustable calibration apparatus of FIG. 11. First, the aperture is positioned so that it is centered on a lenslet that is closest to a center or other desired portion of the Hartmann-Shack spot image, step 61. Optionally, the cross aperture may be continued to be adjusted until the cross aperture is closely aligned to the center of the Hartmann-Shack image and the intensity of the Hartmann-Shack spots in the rows and columns (or other portions of the spot pattern) are more evenly balanced, step 63. Once the calibration apparatus is centered in the Hartmann-Shack image, a marker that has a substantially same shape as the aperture in the calibration apparatus is moved from a center of the image and overlayed with the aperture in the image from the pupil camera, step 65. For the embodiment of FIG. 10, the marker is in the shape of a crosshair which substantially corresponds to the shape of the cross-shaped aperture. Once the marker is aligned with the aperture, the amount of translational movement and rotational movement needed to align the marker and the image of the aperture in conjunction with any offset of the aperture from the desired portion (e.g., center) of the image in the Hartmann-Shack image may be used to determine the misalignment between the Hartmann-Shack camera and the pupil camera, step 67.

The present invention further provides user interfaces for carrying out methods of the present invention. The user interfaces assist the user in aligning the images of the Hartmann-Shack camera 22 and the pupil camera 24. The user interfaces generated by the present invention may be stored in a storage subsystem and displayed on an output device in the wavefront system. FIGS. 12–17 illustrate various user interfaces and methods of the present invention as used with the calibration apparatus of FIG. 10. One of ordinary skill in the art would recognize that other variations, modifications and alternatives may be used with the present invention. Accordingly, the following description is intended to be illustrative, but not limiting of the scope of the present invention.

Figure 12:
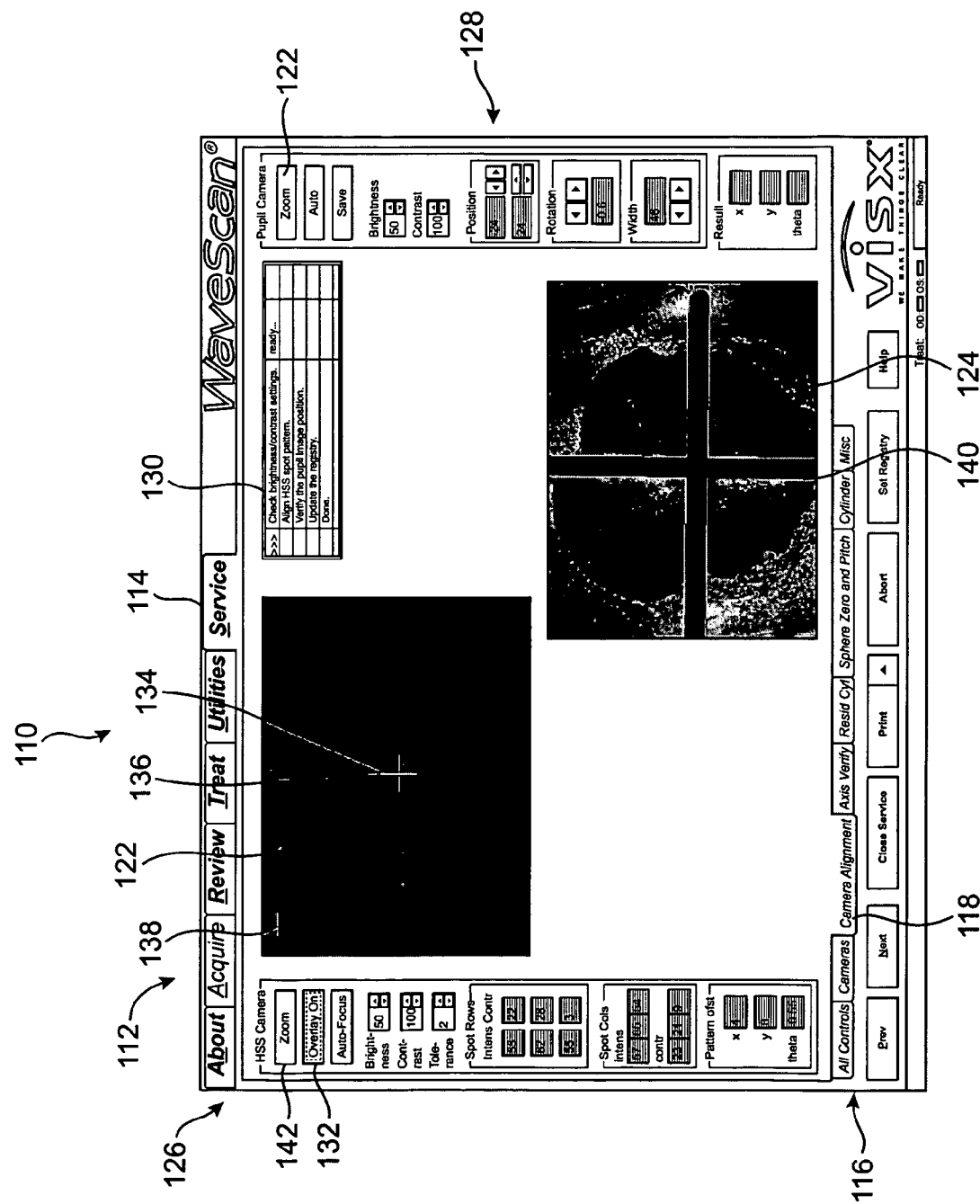
FIGS. 12 to 17 illustrate some graphical user interfaces of the present invention that may be used to carry out the methods of the present invention using the calibration apparatus of FIG. 10.

FIG. 12 illustrates an exemplary user interface 110 for calibrating and aligning the Hartmann-Shack camera 22 and pupil camera 24. In the illustrated embodiment, user interface has a plurality of tabs 112 that allows the user to select the functionality of the software run on the computer system. To calibrate the Hartmann-Shack camera and pupil camera, the user may select or otherwise open a Service Tab 114 (e.g., click on the tab with a cursor or arrow). The Service Tab window allows the user to select a variety of different image parameters, as illustrated by a menu of sub-tabs 116 that are displayed near a bottom of the interface. To align cameras 22, 24, the user may select the "Camera Alignment" tab 118.

User interface 110 may have a window 122 to display the image obtained by the Hartmann-Shack camera and a window 124 to display the image obtained by the pupil camera. Typically, user interface also includes controls 126 for adjusting the Hartmann-Shack camera image and controls 128 for adjusting the pupil camera image. Optionally, user interface 110 may have a window 130 that displays the steps for performing an alignment.

If desired, the user may activate the zoom button 142 so that the either image window 122, 124 occupy the entire center portion of user interface 110. Each image window 122, 124 may be viewed in real-time, frozen, and with overlays.

To begin aligning and registering the images, the user may activate the "Overlay On" button 132 so as to display overlay alignment elements on the displayed window. In the illustrated embodiment, for the Hartmann-Shack image window 122, the alignment elements include a first and second crosshair 134, 136. First crosshair 134 is fixed and may be used to mark a center of the image or any other desired portion of the image. If the software is able to determine a center of the Hartmann-Shack spot pattern, the second crosshair 136 may also be displayed to illustrate the estimated center of the spot pattern. In one configuration, crosshair 134 and crosshair 136 are displayed in different colors (e.g., yellow and blue) and/or are sized differently so as to differentiate the crosshairs from each other. Optionally, a hint arrow 138 may be displayed on the image if the software determines that the Hartmann-Shack image is not centered or if the image is rotated off of the center of the image window.

In the case of the pupil image window 124, an overlay 140 may comprises a cross that corresponds to the shape of the aperture in the calibration apparatus. In some modes, the user may move and re-size the overlay 140 manually. In other modes, the position and size of overlay 140 may be determined automatically by the software.

Figure 13:
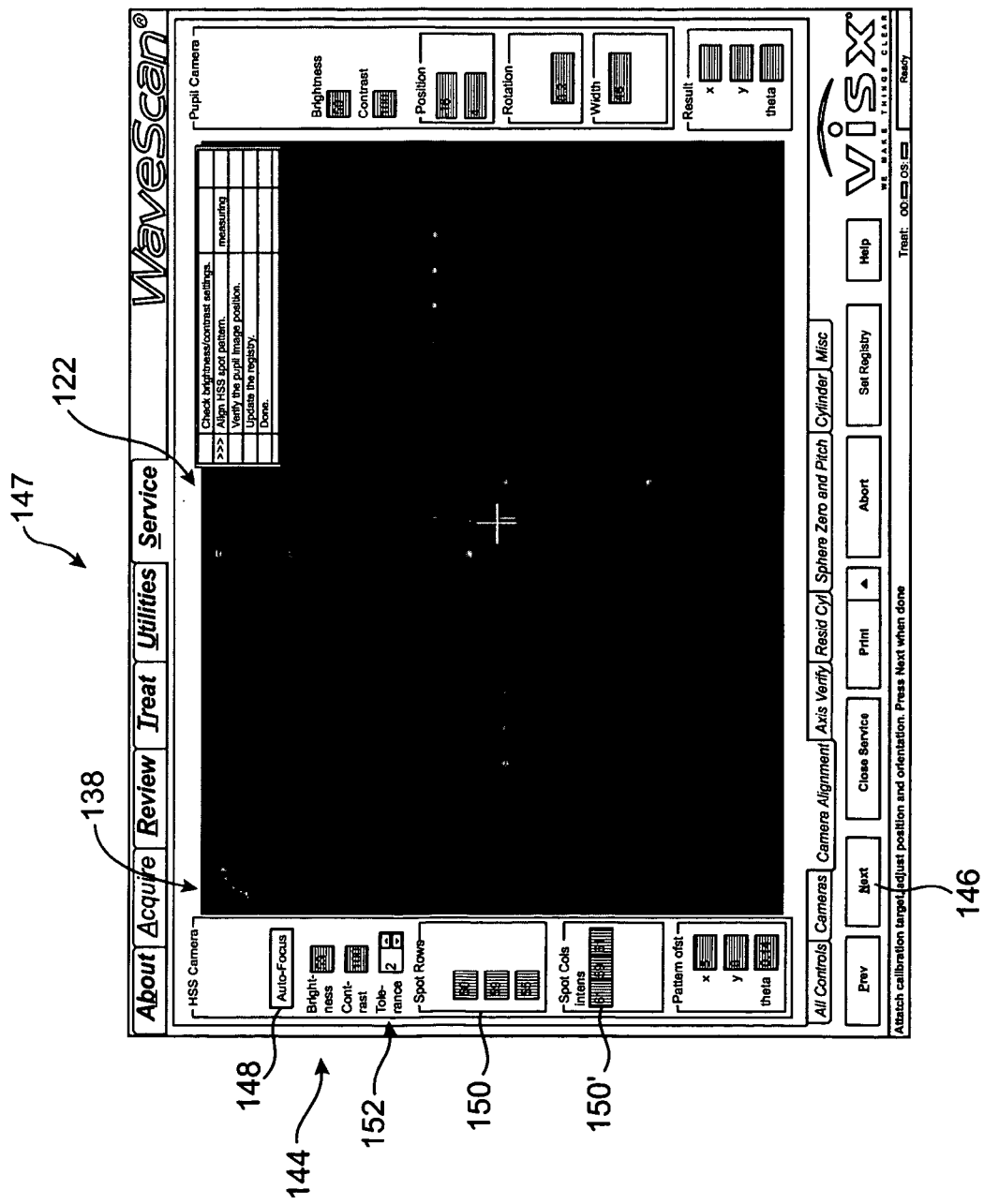
Figure 14:
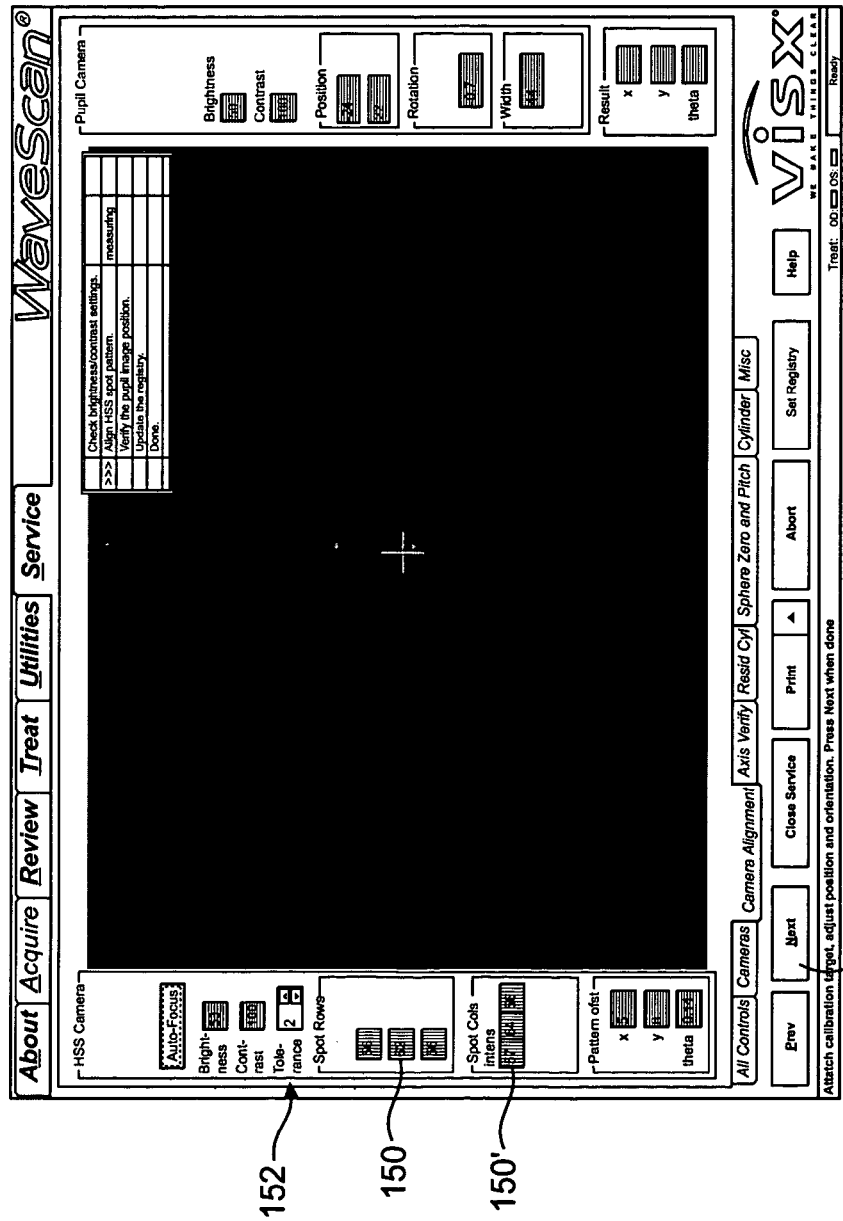

Referring now to FIGS. 13 to 14 image window 122 may be zoomed by actuating zoom button 142 (FIG. 12). To improve the image quality, the user may adjust the contrast and brightness of the image by inputting the desired brightness and contrast into input 144. For example, one useful configuration is a brightness level of approximately 50 and a contrast level of approximately 100. As can be appreciated, depending on the specific image captured, other levels of brightness and contrast may be chosen. Once the brightness and contrast are chosen, the user may press the "Next" button 146.

In a particular usage, in user interface 147, the user may first press the "Auto-Focus" button 148 to focus the image. If the software is able to capture the Hartmann-Shack image, a set of results maybe displayed in text boxes 150, 150' that indicate if the image has been substantially aligned. In one embodiment, the text boxes will be colored to visually indicate if the alignment has been achieved. For example, a red coloration and/or hint arrows 138 may indicate that the image has not yet been aligned (FIG. 13), while a green coloration (and/or no hint arrows) may indicate that the alignment of the image is acceptable (FIG. 14). If the boxes 150, 150' indicate that the image is aligned (e.g., green coloration, no hint arrows 138 on image, or the like), the user may advance to the next user interface by pressing the "Next" button 146.

If boxes 150, 150' indicate that the image is not aligned, the user may manually or automatically adjust the orientation and position of the calibration apparatus so as to substantially center the image of the aperture over the spot pattern so that the image is symmetrical vertically, and horizontally. As shown in FIG. 13, if the software is able to analyze the spot pattern, hint arrows 138 are displayed at the top left of the image window 122 that indicate to the user in which directions the calibration apparatus must be adjusted so as to substantially align a center of the aperture 136 with a center of the Hartmann-Shack image 134 (e.g., up/down, left/right, and/or rotate) so that the center of the Hartmann-Shack Image and the center of the aperture (e.g., crosshairs 134, 136) are substantially aligned.

As is illustrated in boxes 150, 150', boxes 150 are stacked vertically and display numerical results that correspond to the mean intensities of the three central rows of spots. Boxes 150' that are stacked horizontally correspond to the mean intensities of the three central columns of spots. The user may adjust the positioning and orientation of the calibration apparatus until the intensities in the outer rows and columns are more evenly balanced. As shown in FIG. 14 in interface 149, when the Hartmann-Shack image of the aperture is aligned with a center of the image and the intensities of the outer rows are more evenly balanced, the first and last number in each block of 150, 150' should be substantially equal. As may be appreciated, if desired, the user may specify a small count difference by setting a tolerance in the Tolerance control input 152, so as to not require the numbers to be exactly equal. As may be seen in FIG. 14, in the "Pattern ofst" box in the lower left corner of the user interface, the displacement and angular offset of the lenslet array center (e.g., center of image) with respect to a center of the aperture of the calibration apparatus is calculated automatically.

Once the pattern on the Hartmann-Shack image window 122 is sufficiently aligned, the user may press the "Next" button 146, which causes the software to switch to and display the pupil camera image 124 on user interface 154. In one embodiment, the software may be configured to automatically attempt to locate the vertical and horizontal aperture sections. A yellow overlay 140 will indicate the position of the aperture 20 as determined by the software. Alternatively, the user may manually use controls 128 in the right panel to adjust the position, angular orientation, and width of the crosshair overlay 140 from a nominal position (e.g., a center of the image) so as to position the overly 140 over the image of the aperture. The software may calculate the translational and rotational offset from the nominal position. Once the user determines that the overlay is properly positioned, the user may press the Next button 146 to advance to the user interface 156 illustrated in FIG. 16, wherein the software will calculate the positional and angular offsets between the Hartmann-Shack camera and pupil camera, as described above.

The analysis of the images provides information as to the displacement from a center of the images in both of the cameras. Since the absolute location of the aperture is the same in both cases (e.g., simultaneous imaging of a single aperture), the software is able to determine the relative x, y, and θ coordinates of the Hartmann-Shack camera relative to the pupil camera. Because the analysis started out by choosing a specific Hartmann-Shack spot as its center and centered the aperture on that spot, the software also knows the absolute position of the Hartmann-Shack pattern and the angular orientation of the pattern with respect to the Hartmann-Shack camera.

Figure 15:
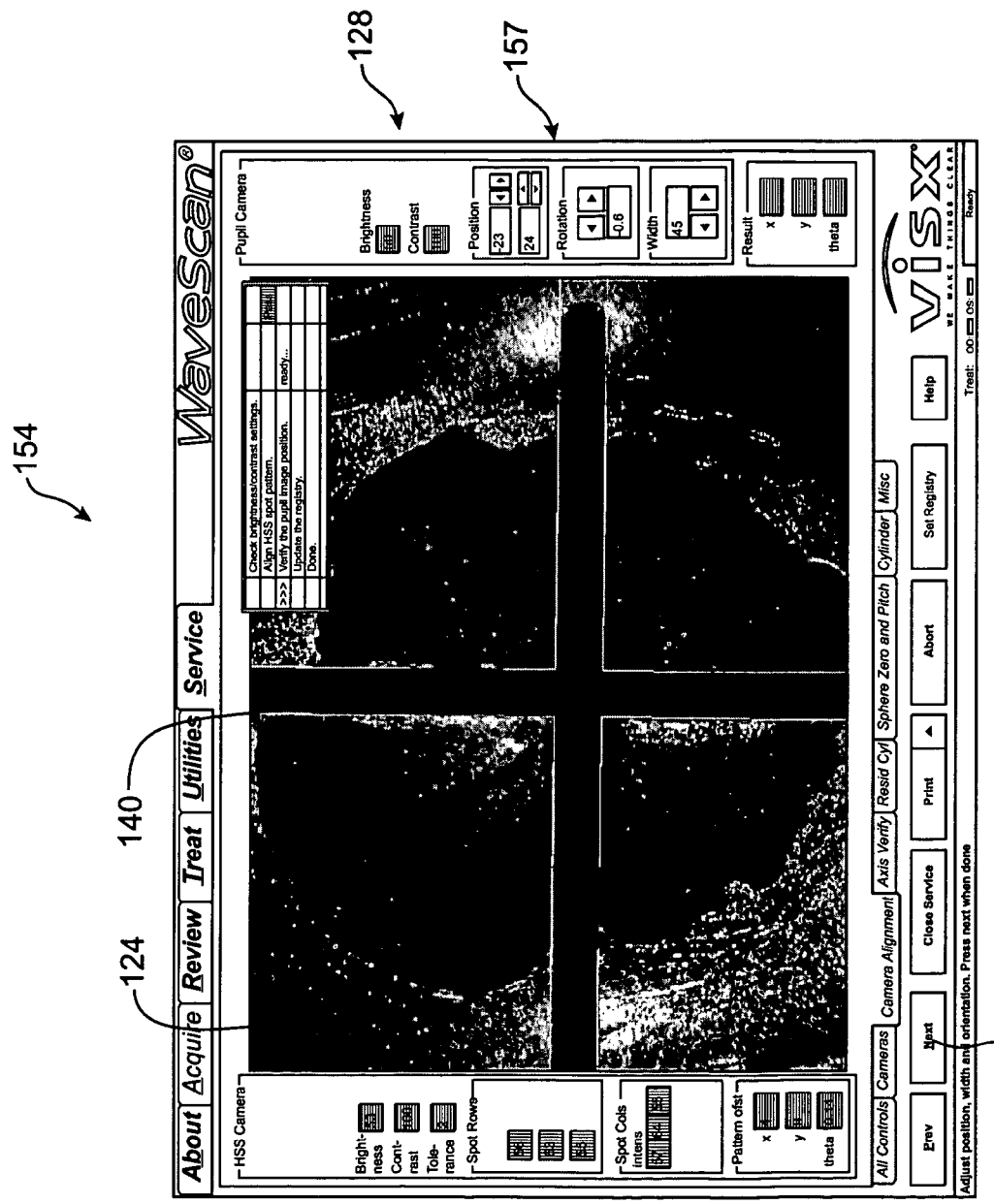
Figure 16:
Figure 17:
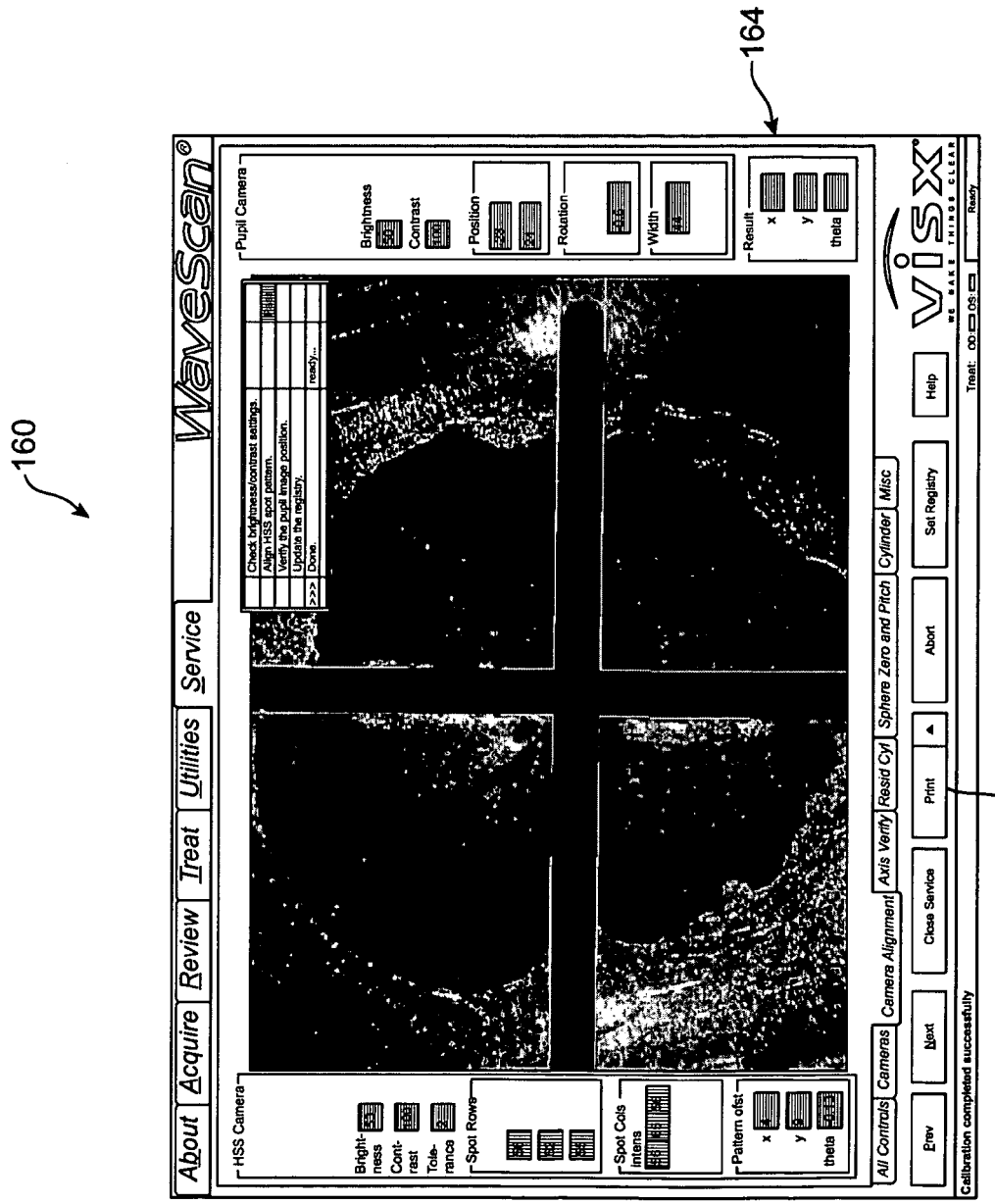

As may be seen in FIGS. 15 and 16, the, numerical data in the Position and Rotation Boxes 157 indicate the relative position and angular rotation of the overlay in the coordinates of the pupil camera so as to indicate the pixel and angle difference from a center of the pupil camera image. To set the alignment parameters between cameras 22, 24, the user may press the "Set Registry" button 158 that actuates the calculation of the offset between cameras 22, 24, as described above. Once the Set Registry 158 button is pressed, the software calculates the misalignment between cameras 22, 24 as described above, and advances to user interface 160 (FIG. 17), in which the calibration is finished. Optionally, the translational and angular offset of the two cameras may be displayed in the Result box 164 of the user interface. If desired, the user may press a "Print" button 162 to obtain a hard copy of the calibration. In the illustrated embodiment, the offset data may be displayed in the "Result" portion on the lower right side of the user interface.

As will be understood by those of skill in the art, the present invention may be embodied in other specific forms without departing from the essential characteristics thereof. For example, the specific set up of the graphical user interfaces are merely examples and should not limit the present invention. Moreover, while the methods may describe a particular order of analyzing the Hartmann-Shack image and pupil camera image, any order of analysis may be performed, and the present invention is not limited to a particular order of analysis. The above examples are merely illustrative of some embodiments that incorporate the present invention and do not limit the scope of the invention. One of ordinary skill in the art would recognize other variations, modifications and alternatives. Accordingly, the foregoing description is intended to be illustrative, but not limiting, of the scope of the invention which is set forth in the following claims.

What is claimed is:

1. A method for measuring a rotational and positional offset between a first imaging device and a second imaging device, the method comprising:
    obtaining an image of a fixture with the first and second imaging device, wherein the first imaging device comprises a Hartmann-Shack camera;
    superimposing a marker in a nominal position over the images of the fixture taken with the first and second imaging device;
    moving the marker from the nominal position in the image obtained with the first imaging device to a position that is substantially aligned with the images of the fixture;
    moving the marker from the nominal position in the image obtained with the second imaging device to a position that is substantially aligned wit the images of the fixture; and
    comparing movement information of the marker in the first image with movement information of the marker in the second image to determine the rotational and positional offset between the first and second imaging devices.

2. The method of claim 1 wherein the movement information comprise at least one of a translation along an x-axis, a translation along a y-axis, and a rotation about a z-axis.

3. The method of claim 1 wherein the fixture comprises a rotationally asymmetric aperture.

4. The method of claim 3 wherein a shape of the marker substantially corresponds to the shape of the rotationally asymmetric aperture in the fixture.

5. The method of claim 1 wherein the first imaging device comprises a Hartmann-Shack camera.

6. The method of claim 1 wherein the nominal positions in the images are a center of the images.

7. A system comprising:
    an imaging system comprising a Hartmann-Shack camera and a pupil camera;
    a calibration apparatus comprising an aperture that is positionable in an optical path of the Hartmann-Shack camera and pupil camera; and
    a control system coupled to the imaging system, wherein the control system is configured to have a first mode and a second mode, wherein the control system in the first mode superimposes a marker in a nominal position over an image of the calibration apparatus taken with the Hartmann-Shack camera through the aperture and an image taken with the pupil camera of the aperture and allows the marker to be moved into substantial alignment with the image of the aperture, wherein the control system in the second mode compares the movement of the marker in the image taken with the Hartmann-Shack camera with the movement of the marker in the image taken with the pupil camera so as to determine the positional and rotational offset between the Hartmann-Shack camera and the pupil camera.

8. The system of claim 7 wherein the aperture is rotationally asymmetric.

9. The system of claim 7 wherein the asymmetric aperture is approximately cross shaped.

10. The system of claim 7 wherein the imaging system is a wavefront system.

11. The system of claim 7 wherein the fixture comprises a non-reflective central portion to prevent reflections.

12. The system of claim 7 comprising a target disposed in the optical axis of the imaging system, wherein the calibration apparatus is positioned between the target and the imaging system.

13. A method for determining relative positional and rotational offsets between a first imaging device and a second imaging device of a system, the method comprising:
providing a body comprising a rotationally asymmetric aperture in an optical path of the first imaging device and a second imaging device;
directing light through the rotationally asymmetric aperture to the first imaging device and second imaging device;
imaging the aperture with the first imaging device and the second imaging device, the image obtained by the first imaging device comprising a spot pattern that corresponds to a shape of the rotationally asymmetric aperture; and
comparing the rotational and positional offsets of the images of the aperture to determine a relative positional end rotational offset between the first and second imaging devices.

14. The method of claim 13 wherein directing comprises reflecting light off of a reflective surface of a target.

15. The method of claim 13 wherein comparing comprises:
superimposing a marker over the image obtained with the first imaging device, wherein the marker substantially corresponds with a shape of the aperture;
moving the marker from a nominal position into substantial alignment with the aperture;
calculating the movement of the marker along the x-axis, y-axis, and rotation about the z-axis;
superimposing a marker over the image obtained with the second imaging device, wherein the marker substantially corresponds with a shape of the aperture;
moving the marker from a nominal position into substantial alignment with the aperture;
calculating the movement of the marker along the x-axis, y-axis, and rotation about the z-axis; and
subtracting the calculated movement of the marker in the image obtained with the first imaging device with the movement of the marker in the image obtained with the second imaging device.

16. A computer program product stored on a computer readable storage medium for registering a first imaging device with a second imaging device, the computer program product comprising machine-readable instructions to perform steps including:
obtaining images with the first imaging device and second imaging device;
superimposing a marker over the images of the fixture taken with the first and second imaging device, the image obtained by the first imaging device comprising a spot pattern that corresponds to a shape of the rotationally asymmetric aperture;
moving the marker in the image obtained with the first imaging device to substantially align the marker with the fixture;
moving the marker in the image obtained with the second imaging device to substantially align the marker with the fixture;
comparing the movement information of the marker in the first image with the movement information of the marker in the second image to determine the rotational and positional offset between the first and second imaging devices.

17. A method of registering a first imaging device with a second imaging device, the first imaging device comprising a Hartmann-Shack camera, the method comprising:
positioning a fixture so that the fixture is imaged by the first imaging device and second imaging device, the fixture comprising a body comprising an aperture, the image obtained by the first imaging device comprising a spot pattern that corresponds to a shape of the aperture; and
analyzing the images of the fixture obtained by the first imaging device and the second imaging device to determine a misalignment between the first imaging device and the second imaging device.

18. The method of claim 17 comprising adjusting the position of the fixture so that the fixture is positioned in a desired position in the image obtained by the first imaging device.

19. The method of claim 18 wherein adjusting the position comprises changing at least one of an angular orientation and translational position of the fixture within an optical axis of the first imaging device.

20. The method of claim 18 wherein the desired position is substantially a center of the image obtained byte first imaging device.

21. The method of claim 20 wherein analyzing the images comprises calculating a translational and angular offset of the fixture from a center of the image obtained by the second imaging device.

22. The method of claim 21 wherein calculating comprises:
moving a marker from a center of the image obtained by the second imaging device until the marker in substantially aligned with the fixture; and
measuring an amount of translational movement and angular movement needed to substantially align the marker with the fixture.

23. The method of claim 17 comprising adjusting at least one of a position and angular orientation of the aperture until an intensity in selected portions of the spot pattern are substantially evenly balanced.

24. The method of claim 17 wherein the aperture is asymmetrically shaped, wherein the asymmetrically shaped aperture of the fixture and the marker comprise substantially same shapes.

25. The method of claim 24 wherein the shaped aperture is cross shaped.

26. A method for measuring a rotational and positional offset between a first imaging device and a second imaging device, the method comprising:

obtaining an image of a fixture with the first and second imaging device, the fixture comprising a rotationally asymmetric aperture having a shape, the image obtained by the first device comprising a spot pattern that corresponds to a shape of the rotationally asymmetric aperture;

superimposing a marker in a nominal position over the images of the fixture taken with the first and second imaging device, a shape of the marker substantially corresponding to the shape of the rotationally asymmetric aperture in the fixture;

moving the marker from the nominal position in the image obtained with the first imaging device to a position that is substantially aligned with the images of the fixture;

moving the marker from the nominal position in the image obtained with the second imaging device to a position that is substantially aligned with the images of the fixture; and comparing movement information of the marker in the first image with movement information of the marker in the second image to determine the rotational and positional offset between the first and second imaging devices.

* * * * *